United States Patent
Hahn et al.

(10) Patent No.: US 6,273,717 B1
(45) Date of Patent: Aug. 14, 2001

(54) DENTAL INSTRUMENT FOR SONIC OR ULTRASONIC TREATMENT

(75) Inventors: Rainer Hahn, Tübingen; Uwe Grotz, Löchgau, both of (DE)

(73) Assignee: Durr Dental GmbH & Co. KG (DE)

( * ) Notice: Subject to any disclaimer, the term of this patent is extended or adjusted under 35 U.S.C. 154(b) by 0 days.

(21) Appl. No.: 09/546,922

(22) Filed: Apr. 11, 2000

(30) Foreign Application Priority Data

Apr. 11, 1999 (DE) .................................. 199 16 156

(51) Int. Cl.[7] ................ A61C 1/07; A61C 3/03; A61C 3/08
(52) U.S. Cl. .................................. 433/119; 433/165
(58) Field of Search ..................... 433/118, 119, 433/165, 141

(56) References Cited

U.S. PATENT DOCUMENTS

3,937,990 * 2/1976 Winston .................................. 310/8.3

* cited by examiner

Primary Examiner—Nicholas D. Lucchesi

(57) ABSTRACT

A dental instrument for sonic or ultrasonic treatment comprises a shank (1) to which a treatment section (2) is joined. The shank (1) and treatment section.(2) are made of matrix-bonded carbon fibers. The instrument can be machined out of a woven carbon fiber fabric or can be a compression molding or an injection molding. The mechanical properties of the instrument can be adjusted by varying the length of the carbon fibers.

15 Claims, 1 Drawing Sheet

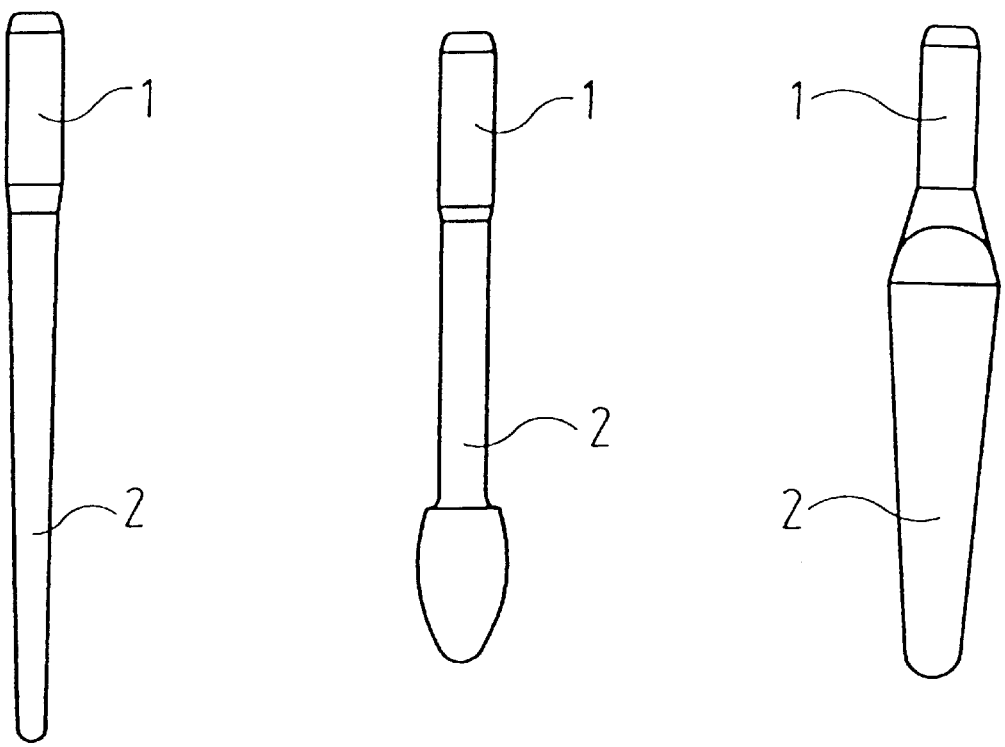
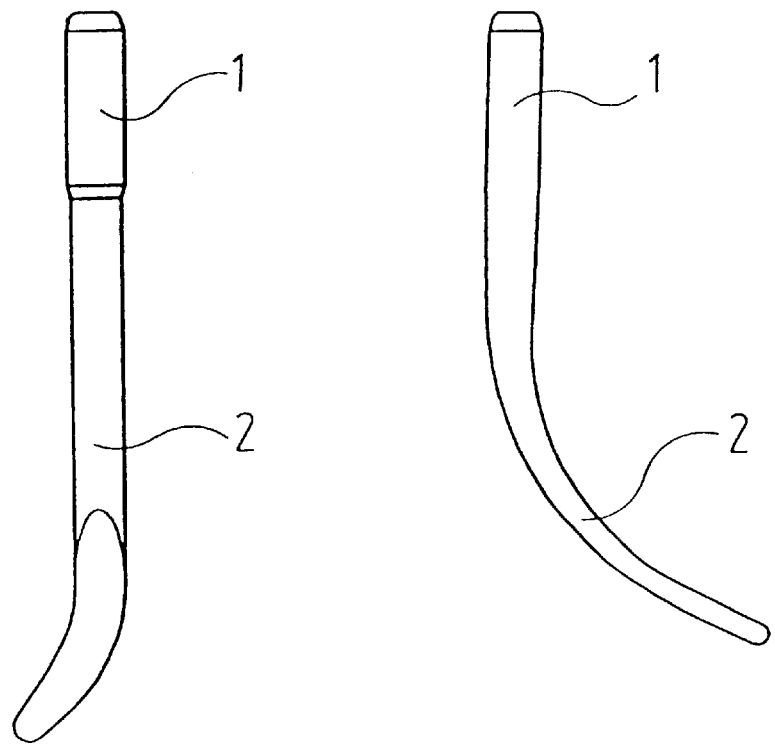

DENTAL INSTRUMENT FOR SONIC OR ULTRASONIC TREATMENT

The invention relates to a dental instrument for sonic or ultrasonic treatment, comprising a shank and a treatment section joined thereto.

The advantages associated with sonic or ultrasonic treatment, especially for periodontal diseases, tooth cleaning or periimplantitis therapy, have gained increasing recognition in recent times. In this treatment, a treatment instrument subjected to sonic or ultrasonic vibrations, which is irrigated by a fluid, is introduced into the patient's dental pockets. This generally requires a whole range of instruments of different shapes and sizes.

The known and currently used dental instruments of the type mentioned at the outset are made of metal. Where ultrasonic treatment is concerned, conventional metal instruments result in a pronounced energy contact and are rigid and inflexible, so they tend to be of limited use on tooth surfaces with complex curvatures. In the case of prophylactic treatment or tooth cleaning, they leave blackish abraded material behind, especially on ceramic dental prostheses. In the case of periimplantitis therapy, the use of metal instruments causes undesired polishing effects on the structurally complex surfaces of the implant.

The object of the present invention is to provide a dental instrument of the type mentioned at the outset which is flexible and has a comparatively soft surface.

This object is achieved according to the invention by means of a dental instrument made of matrix-bonded fibers.

Such instruments not only have a very high abrasion resistance but are also particularly suitable as dental instruments by virtue of their elasticity. With their comparatively soft surface, they leave no abraded material behind on the surfaces of teeth or dental prostheses and do not cause changes on the surfaces of ceramic or metal implants. They wear out slowly and therefore have an optimally adapted shape for a long period of time. The flexibility can be graded by the choice of fiber material and fiber length.

The matrix in which the fibers are bonded is preferably a synthetic resin, e.g. PEEK, polysulfone or acrylate, or a thermoplastic.

A particularly high mechanical stability and breaking strength, combined with very good elasticity properties, is achieved when the length of the fibers is a multiple of the diameter of the instrument.

The dental instrument can be machined out of a woven fiber fabric. Alternatively it can be a compression molding or an injection molding. In the latter case, either the fibers are so short that the mixture of fibers and matrix forms an injectable compound before setting, or the fibers are placed in the injection mold before injection of the matrix.

Particularly in the case of curved instruments, it is advisable for the fibers to be approximately parallel to the longitudinal direction of the instrument.

The dental instruments according to the invention can contain short reinforcing fibers in addition to or instead of the fibers already mentioned above.

Furthermore, the dental instruments according to the invention can contain inorganic particles, e.g. glasses, ceramic particles, phosphate particles or apatite particles, in addition to or instead of the fibers. Said particles serve either as a reinforcement or as passive particles which, under working conditions, are dissolved out of the instrument and are used to modify the surfaces, e.g. for improved polishing effects.

Embodiments of the invention are illustrated in greater detail below with the aid of the drawing. The single Figure shows a range of dental treatment instruments in profile.

All the dental instruments shown in the drawing have a cylindrical shank 1 to which treatment sections 2, each of a different shape, are joined. Substantially linear treatment sections 2 are shown in the top row of the drawing and curved treatment sections 2 are shown in the bottom row of the drawing.

The instrument shown on the left of the top row of the drawing is a linear probe for buccolingual or palatal surfaces of teeth or roots and is used in the course of periodontal treatment, tooth cleaning, periimplantitis therapy or periodontal prophylaxis. The instrument shown in the middle of the top row has a bud-shaped enlargement at the end of the treatment section 2 and is used especially for cleaning concave tooth surfaces. The instrument shown on the right of the top row is spade-shaped and is used for the cleaning, treatment or prophylaxis of approximal tooth surfaces in the course of tooth cleaning, periodontal treatment or periodontal prophylaxis.

On the left of the bottom row, the drawing shows a curette-shaped instrument used for treating the approximal root surfaces in the course of periodontal treatment or periodontal prophylaxis. Finally, on the right of the bottom row, the drawing shows a curved probe for furcated regions of the teeth or roots; it is also used for periodontal treatment or periodontal prophylaxis.

For use, the dental instruments are gripped by their shank 1 in the clamping device of a sonic or ultrasonic treatment apparatus and caused to vibrate by a sonic or ultrasonic vibrator, the main direction of vibration being the longitudinal direction of the instrument. The curved treatment sections 2 of the instruments illustrated in the bottom row additionally execute a wiper-like motion, enhancing the desired effect.

During use, the dental instruments are irrigated by water, an aqueous solution or an aqueous slurry, the last of these containing abrasive particles. It is easy to understand that, under these use conditions, exacting demands are made on the dental instruments and the risk of wear is very high.

In a first process for the manufacture of the dental instruments, a woven fabric is initially produced from carbon fibers of appropriate length and this fabric is then impregnated with the synthetic resin matrix. The rough shapes of the instruments are sawn out of the resulting fiber mat and then machined into the final shape by milling or by turning on a lathe.

An alternative method of manufacture consists in placing the carbon fibers in a compression mold (in this case the fibers can extend over virtually the entire length of the instrument), filling the mold with the synthetic resin, closing the mold and then curing the product under pressure. In this embodiment the carbon fibers run parallel to the longitudinal direction of the dental instrument, which can be very advantageous in terms of the elasticity of the treatment section in particular.

The following manufacturing process is more cost-effective:

The carbon fibers are cut into short lengths so as to form an injectable compound together with the matrix-forming synthetic resin. Then, analogously to a homogeneous plastic, they are injected into a mold which determines the shape of the instrument.

What is claimed is:

1. A dental instrument for sonic and ultrasonic treatment for periodontal diseases, tooth cleaning and periimplantitis therapy, comprising a shank and a treatment section joined thereto, which instrument is made of matrix-bonded fibers, is flexible and sized so that it can be introduced into a patient's dental pockets.

2. A dental instrument as claimed in claim 1 wherein the fibers are glass fibers, carbon fibers, metal fibers or organic fibers.

3. A dental instrument as claimed in claim 2, wherein the glass fibers are silanized glass fibers.

4. A dental instrument as claimed in claim 1, wherein the matrix is a synthetic resin, or a thermoplastic.

5. A dental instrument as claimed in claim 4, wherein the synthetic resin is one of PEEK, polysulfone or acrylate.

6. A dental instrument as claimed in claim 4, wherein the synthetic resin is PEEK, polysulfone or acrylate.

7. A dental instrument as claimed in claim 1 wherein the length of the fibers is a multiple of the diameter of the instrument.

8. A dental instrument as claimed in claim 1, wherein said dental instrument comprises machined woven fiber fabric.

9. A dental instrument as claimed in claim 1 wherein said dental instrument comprises a compression molding.

10. A dental instrument as claimed in claim 1 wherein said dental instrument comprises an injection molding.

11. A dental instrument as claimed in claim 1 wherein the direction of the fibers is parallel to the longitudinal direction of the instrument.

12. A dental instrument as claimed in claim 1 which contains short reinforcing fibers.

13. A dental instrument as claimed in claim 1, which contains inorganic particles.

14. A dental instrument as claimed in claim 13, wherein the inorganic particles are glasses, ceramic particles, phosphate particles or apatite particles.

15. A dental instrument as claimed in claim 1, wherein said treatment section is selected from the group consisting of a treatment section having the form of a linear probe, a treatment section having a bud-shaped enlargement at the end of the treatment section, a treatment section which is spade-shaped, a treatment section which is curette-shaped and a treatment section in the form of a curved probe.

* * * * *